(12) United States Patent
Termanini

(10) Patent No.: US 8,167,883 B2
(45) Date of Patent: May 1, 2012

(54) OSCILLATING BONE CHIPPER

(76) Inventor: Zafer Termanini, Cedar Grove, NJ (US)

( * ) Notice: Subject to any disclaimer, the term of this patent is extended or adjusted under 35 U.S.C. 154(b) by 268 days.

(21) Appl. No.: 12/383,023

(22) Filed: Mar. 19, 2009

(65) Prior Publication Data

US 2010/0241125 A1 Sep. 23, 2010

Related U.S. Application Data

(60) Provisional application No. 61/070,230, filed on Mar. 20, 2008.

(51) Int. Cl.
*A61B 17/56* (2006.01)
(52) U.S. Cl. .......................................... 606/83; 606/171
(58) Field of Classification Search .............. 606/79–84, 606/86 R, 87–88, 167–180; 30/43.7–43.8, 30/208–209; 83/490–491, 592, 610–612
See application file for complete search history.

(56) References Cited

U.S. PATENT DOCUMENTS

| 1,763,730 | A | * | 6/1930 | von Lackum | 606/176 |
| 3,526,219 | A | * | 9/1970 | Balamuth | 600/565 |
| 5,228,459 | A | * | 7/1993 | Caspari et al. | 128/898 |
| 6,242,823 | B1 | * | 6/2001 | Griswold | 310/30 |
| 2004/0122436 | A1 | * | 6/2004 | Grimm | 606/87 |
| 2004/0172044 | A1 | * | 9/2004 | Grimm et al. | 606/130 |
| 2006/0149276 | A1 | * | 7/2006 | Grimm | 606/88 |
| 2006/0200152 | A1 | * | 9/2006 | Karubian et al. | 606/82 |

* cited by examiner

*Primary Examiner* — Thomas C. Barrett
*Assistant Examiner* — Larry E. Waggle, Jr.
(74) *Attorney, Agent, or Firm* — Samir Termanini, Esq.

(57) ABSTRACT

Improved method for removing large amount of bone and articulate surface including cartilage comprising a bone chipper, which can be adapted for usage with any large articular surface or bony structure through a small incision using minimally invasive surgical approach. The inventive device includes an oscillating chipper tip having a series of metallic blades with sharp cutting edges vertically situated and attached to a metallic circular platform. Said platform is situated at the distal end of shank blade. The circular platform and cutting blade will oscillate horizontally driven by the reciprocating eccentric cam with his attached proximally to a reciprocating central shaft. Each of the vertical blades has two sharp vertical cutting edges. The blade shank contains a suction channel, which allows of the removal of bone particles and tissue debris generated by the cutting process. The electromagnetic driver comprises three or four electromagnetic coils placed in a collinear fashion and in series. The coils being separated by magnetic Neodymium wafers firmly attached to the reciprocating central shaft which actually move back and forth driven by the electromagnetic coils as they receive alternating current from a frequency modulator external power supply unit. A railing in the form of an inverted T located at the bottom of the electromagnet driver and used to guide the movement of the driver when said guide slides into corresponding T grooves located on the femoral and tibial templates which are positioned adjacent to the tibial and femoral bones and firmly secured by two or more large guide wires inserted through the templates and into the bone.

6 Claims, 7 Drawing Sheets

OSCILLATING BONE CHIPPER

CROSS-REFERENCE TO RELATED APPLICATIONS

This Application claims benefit of U.S. Provisional Patent Application 61/070,230 filed Mar. 20, 2008, which is hereby incorporated by reference in its entirety.

STATEMENT REGARDING FEDERALLY SPONSORED RESEARCH OR DEVELOPMENT

Not applicable.

FIELD OF THE INVENTION

The present invention relates generally to handheld bone saw and chipper and more specifically it relates to an oscillating bone chipper and cutter for cutting and removing large amount of bone and articular surface including articular cartilage mainly from the knee joint but can be adapted for usage with any large articular surface through a small incision using minimal surgical approach.

BACKGROUND OF THE INVENTION

It can be appreciated that bone saws and devices such as burrs have been in use for many years. Typically bone saws are comprised of oscillating or reciprocating thin metallic blades driven by portable hand units powered by compressed gas or battery operated.

The main problem with conventional saws and burrs is the excessive wandering of the tip of the blades during the oscillatory cycle, which can cause cutting, shredding or extensive contusions to the surrounding tissues. This issue becomes critical when maneuvering the conventional blades and burrs in very tight spaces. Another problem with conventional small blades is the fact that it is very hard to manually control the tip of the oscillating blade by hand since it is common for the tip to wander and "kick back" in a manner similar to tree chainsaws. In addition, the conventional thin saw blade have tendency to bend when cutting deeply into bone thereby causing a significant error in the cutting process. Another problem with the conventional saw blades is the fact that the bone debris generated from the cutting process are usually disseminated in the wound and further deeply spread into the wound by the irrigation process. The prior art teaches devices that provide irrigation channels that inject fluid into a wound (e.g., U.S. Pat. No. 4,008,720 to Brinkmann et al. and U.S. Pat. No. 5,122,142 to John Pascaloff). However these patents fail to provide a suction channel for removal of bone and tissue debris.

While these devices may be suitable for a particular purpose to which they address, they are not suitable for removing large amount of bone and articular surface including cartilage, more specifically from the knee joint but can be adapted for usage with any large articular surface or other bony structure through a small incision using minimal surgical approach. The main problem with the conventional bone saws and burrs is the excessive excursion of the tip of the cutting blade or bur during the oscillatory cycle is excessive and can cause cutting, shredding or extensive contusions of the surrounding tissues adjacent to the operated surface. This becomes critical when maneuvering these conventional devices in very tight anatomical spaces or through small surgical incisions.

In these respects, the electromagnetic oscillating bone chipper and saw according to the present invention substantially departs from the conventional concepts and design of the prior art, and in so doing provides an apparatus primarily developed for the purpose of removing large amount of bone and articular surface including cartilage and soft tissue mainly from the knee joint but can be adapted for use with any large articular surface through a small incision using minimal surgical approach. Furthermore, the presence of a suction channel allow the removal of bone debris generated by the cutting process.

SUMMARY OF THE INVENTION

In view of the foregoing disadvantages inherent in the known type of bone cutting and burring devices now present in the prior art, the present invention provides a new bone cutting device operated by an electromagnetic driver in order to attain high rate of speed and oscillation, wherein the same can be utilized for removing large amount of bone and articular surface from the knee joint but can be adapted for usage with any large articular surface through a small incision using minimally invasive surgical approach.

The general-purpose of the present invention, which will be described subsequently in greater detail, is to provide a new device comprising an oscillating bone chipper that has many of the advantages of the existing bone cutting devices mentioned heretofore and many novel features that result in a new method which is not anticipated, rendered obvious, suggested, or even implied by any of the prior art either alone or in any combination thereof.

To attain this, the present invention generally comprises an oscillating chipper tip having a metallic circular platform with several vertical blades. Each blade having two sharp cutting edges one on each side, and vertically situated at the periphery of a metallic platform. Said platform and vertical blades oscillate horizontally and articulate with the supporting shank and are driven by a reciprocating cam situated longitudinally within the hollow body of the supporting shank that contains a suction channel that allows the removal of bone particles and tissue debris generated by the cutting process.

The electromagnetic driver comprises three or four coils linearly situated and connected in series, having a hollow center and firmly attached to the body of the driver. Said coils are separated by wafers of magnetic Neodymium which are firmly attached to a central reciprocating shaft whereby magnetic force generated by the coils drive said shaft back and forth. The coils are powered by an external power supply and the frequency modulator unit. The electromagnetic driver has a railing at the bottom of the unit in a form of an inverted T to guide their movement of the driver when said rail slide into a T groove located on the femoral and tibial cutting guides or templates. The femoral and tibial templates are positioned against the tibia and femur and firmly secured by placing large guide wires passing through the templates into the bone.

There has thus been outlined, rather broadly, the more important features of the invention in order that the detailed description thereof may be better understood, and in order that the present contribution to the art may be better appreciated. There are additional features of the invention that would be described hereinafter.

In this respect, before explaining the preferred embodiments of the present invention in detail, it is to be understood that the invention is not limited in its application to the details of construction and arrangement of its components set forth in the following descriptions, or illustrations. Also it is to be understood that the phraseology and terminology employed herein are for the purpose of the description and should not be regarded at limiting.

A primary object of the present invention is to provide an electromagnetic oscillating bone chipper that will overcome the shortcomings of the prior art devices. Said device would be capable of removing large amount of bone and articular surface including cartilage and soft tissue mainly from the knee joint but can be adapted for usage with any large articular surface or bony mass through a small incision using minimally invasive surgical approach. It is to be understood that the number of the blades, thickness and height varies with the size of the circular platform and the amount of bone intended to be removed.

Other objects and advantages of the present invention will become obvious to the reader and it is intended that these objects and advantages are within the scope of the present invention.

To the accomplishment of the above and related objects, this invention may be embodied in the form elicited in the accompanying drawings, attention being called to the fact, however, that the drawings are illustrative only and that changes may be made in the specific construction illustrated.

BRIEF DESCRIPTION OF THE DRAWINGS

Various other object, features and attendant advantages of the present invention will become fully appreciated as the same becomes better understood when considered in conjunction with the accompanying drawings, in which the same reference number is used throughout the several views to refer to an identical or similar, wherein.

DETAILED DESCRIPTION OF THE INVENTION

Figure 1:
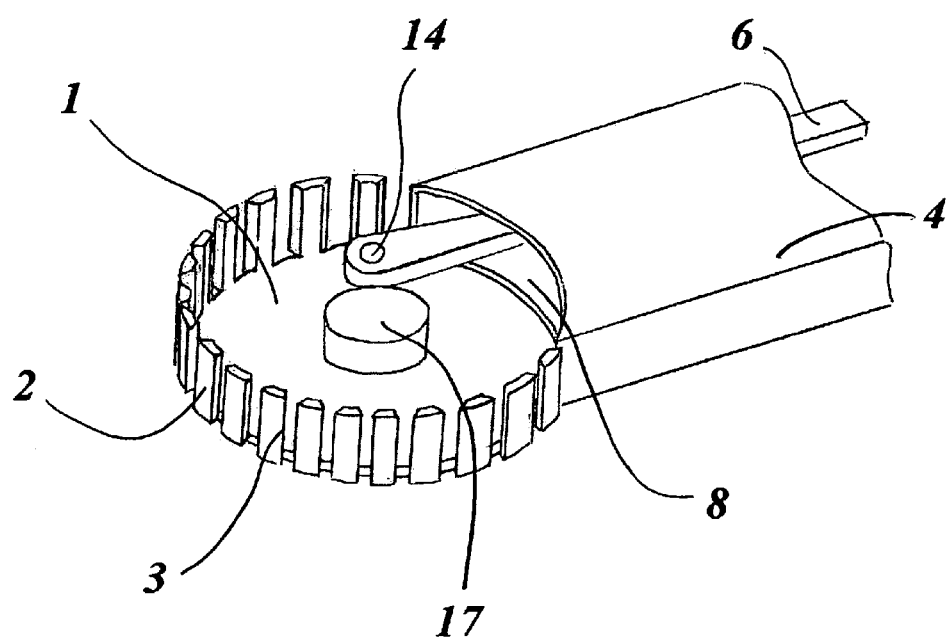
FIG. 1 is perspective view of the cutting blades and platform attachment with the Reciprocating cam.
Figure 2:
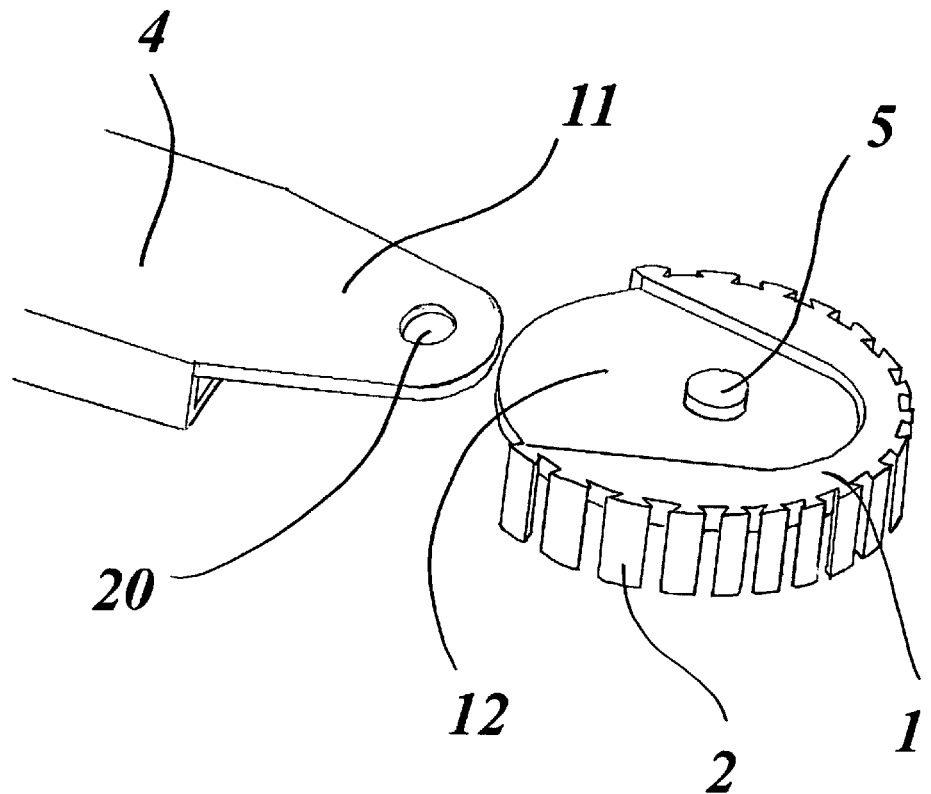
FIG. 2 is perspective bottom view of the oscillating blade attachment and blade shank
Figure 3:
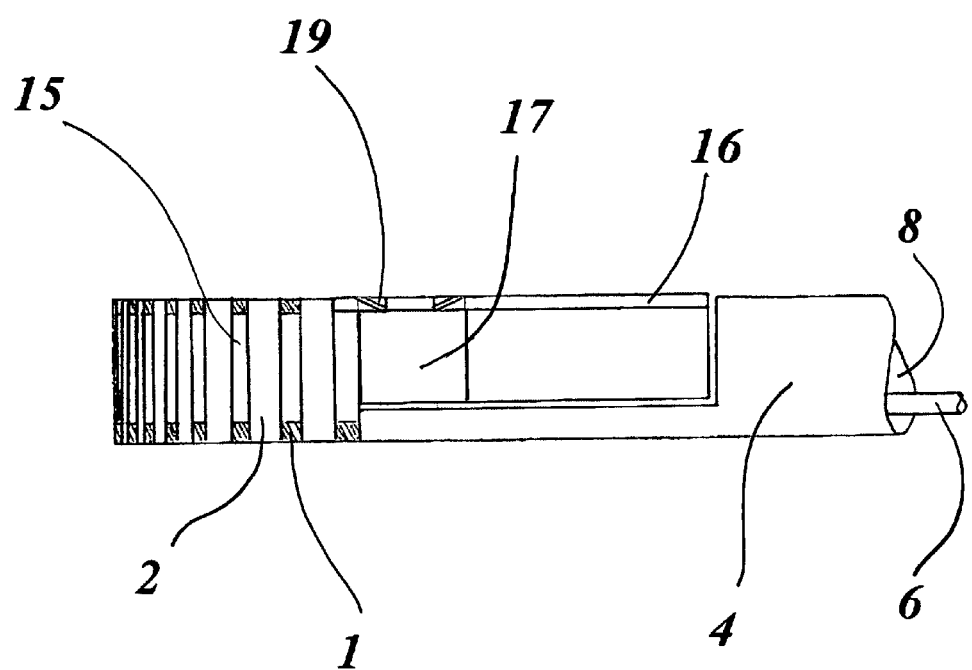
FIG. 3 is perspective side view of the oscillating chipper tip.
Figure 4:
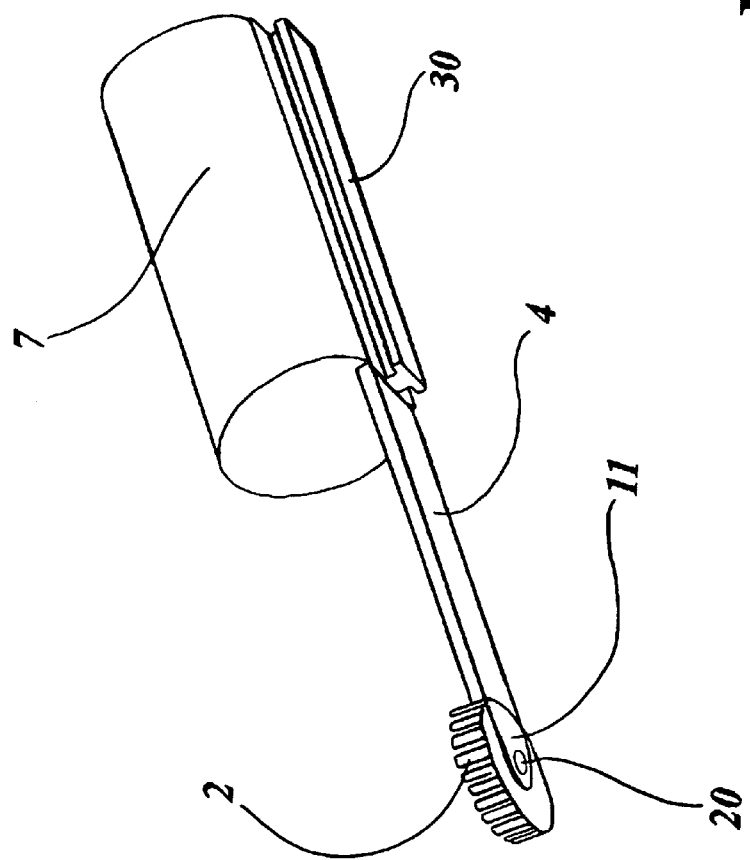
FIG. 4 is perspective view of the cutting blades attached to the electromagnetic Driver.
Figure 5:
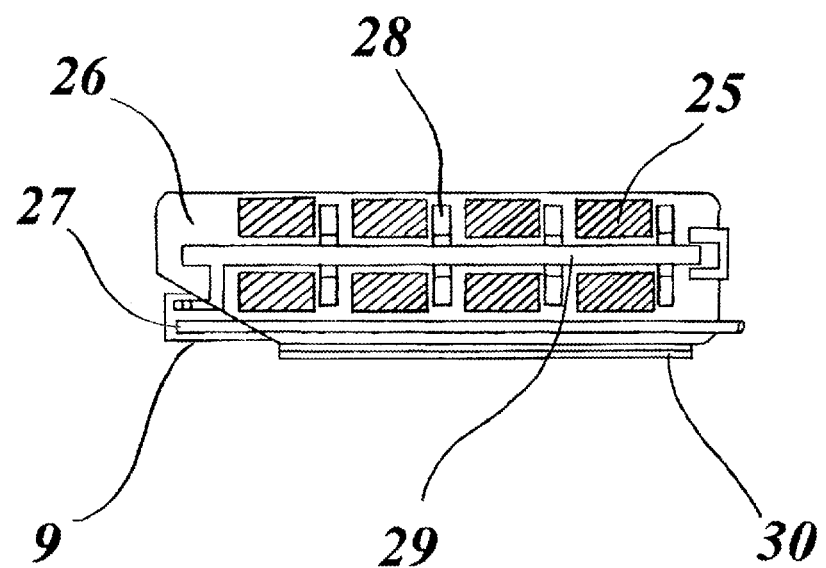
FIG. 5 is a cross-section of the electromagnetic driver.
Figure 6:
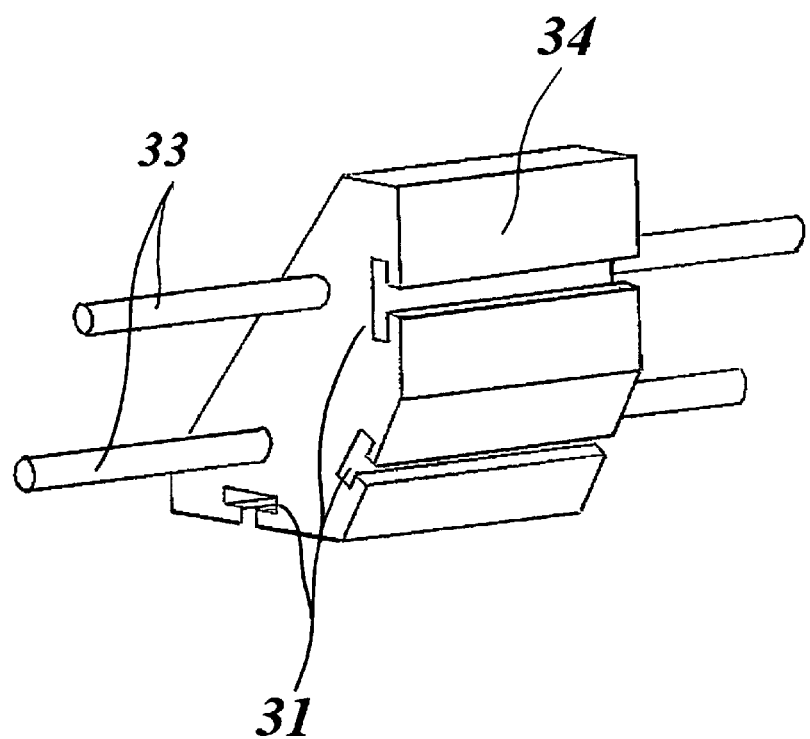
FIG. 6 is a perspective view of the femoral template, T-grooves and lowest fixation pins.
Figure 7:
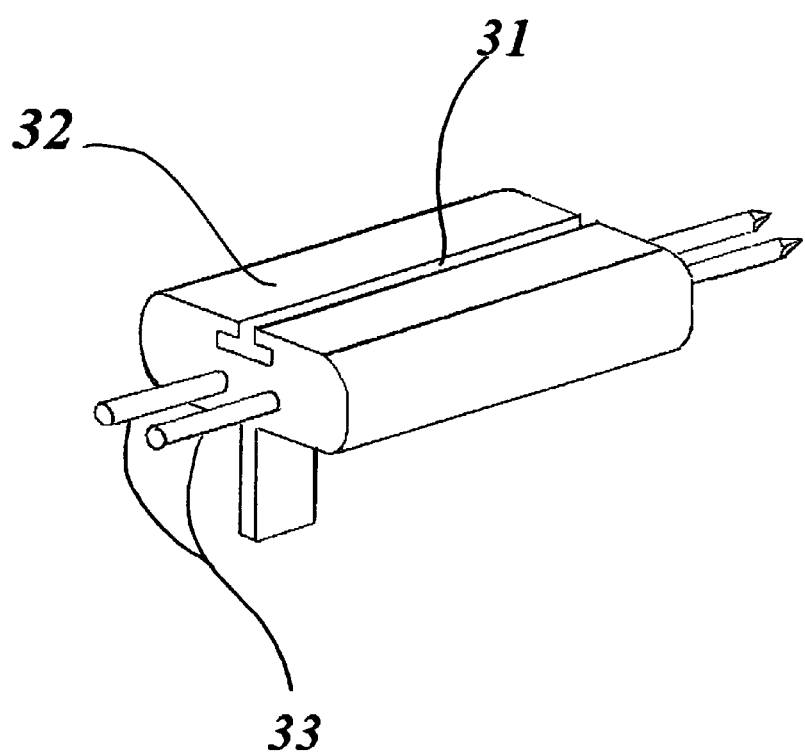
FIG. 7 is a perspective view of the tibia template, T-groove and lowest fixation pins.

Turning now descriptively to the drawing, in which similar references characters denote similar elements throughout the several views, the attached figures illustrate the electromagnetic oscillating bone chipper and cutter, which comprises an oscillating chipper tip having a metallic circular platform (1) to which several vertical blades (2) are firmly attached. Said Blades have sharp cutting edges (3) situated on either side of the vertical blades. The platform is situated at the distal end of a flat shank (4), to which is attached with an axial pin (5). The platform and the vertical cutting blades oscillate horizontally driven by a reciprocating cam (6), which is attached proximally to an electromagnetic reciprocating driver (7). The circular metallic platform has a variable number of blades situated vertically at its periphery. A flat hollow shank connects the reciprocating driver to the circular chipper. The hollow body of the shank provides a suction channel (8), which allows the removal of bone particles and tissue debris generated by the cutting process. In addition, the hollow body of the shank contains the reciprocating cam (6), which connects to the electromagnetic driver (7) through a quick coupling mechanism (9).

More descriptively, the chipper tip consists of a circular metallic platform (1) having a variable number of cutting blades (2) situated vertically at its periphery. Each of the vertical blades has two sharp vertical cutting edges (3). Said platform rotates around an axial central pin (5) located on the bottom surface of the platform and articulates with a corresponding hole (20) located at the end of the tongue (11). Said tongue which is a flat extension of the distal end of the shank will sit in a recessed space (12) at the bottom of the metallic platform in order to obtain a flat design. Furthermore, the metallic platform is attached to a reciprocating cam (6) via a pin (14) eccentrically situated on the top surface of the platform. The reciprocating cam is located flatly within the body of the shank next to the suction channel. The suction channel located within the body of the driver (27) connects bay way of quick connect to the suction channel of the blade shank. The platform and the vertical blades form an enclosure (15) that is covered on the top by a covering plate (16) attached to the central core (17) via central locking pin (19).

The electromagnetic driver comprises three or four coils (25) linearly situated and connected in series, having a hollow center and firmly attached to the body (26) of the driver. Since coils are separated by wafers of magnetic Neodymium (28) which are firmly attached to the central reciprocating shaft (29). Said shaft moves back and forth and driven by the magnetic force of the coils. The coils are powered by an external power supply and frequency modulator unit. The electromagnetic driver have a longitudinal railing at the bottom of the unit (30) in a form of an inverted T to guide the movement of the driver when said rail slide into aT groove (31) located on the femoral and tibial cutting guides or templates. The femoral (34) and tibial (32) templates are positioned against the tibia and femur and firmly secured by placing large guide wires (33) passing through the templates into the bone.

It is to be noted that the number of the vertical cutting blades as well as their height may vary in accordance with the amount of bone to be cut and resected. In addition, the length of the shank blade as well as its thickness may vary to allow the appropriate amount of bone particles and tissue debris to be aspirated by the suction channel.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., if used, are merely labels, and are not intended to impose numerical requirements on their objects.

What is claimed is:

1. A device for chipping bone and articular cartilage through a small incision using minimally invasive surgical approach comprising:

a chipper tip having a metallic circular platform to which a plurality of trapezoidal cutting blades are firmly attached at the periphery of said metallic circular platform whereby said cutting blades stand perpendicular to said metallic circular platform;

a suction channel for removal of bone particles and debris; an electromagnetic reciprocating driver, attached to said chipping tip by way of a quick coupling mechanism wherein said electromagnetic driver is housed in a hollow casting body having a solidary rail at its bottom in a form of inverted T; a femoral and a tibial cutting guide for precision guiding of said electromagnetic driver during bone chipping;

a series of three or more electromagnetic coils having a hollow center;

a series of Neodymium magnets in a form of wafers located between said electromagnet coils;

a reciprocating shaft centrally located and firmly connected at its periphery to said Neodymium wafers;

a flattened blade shank having a tongue;

a central shaft connected by way of quick connect to said reciprocating shaft located in said flattened blade shank; and a suction channel located within the body of the driver connected by way of quick connect to the suction channel of the blade shank.

2. The device in claim 1, further comprising: a flat removable covering disk for removal of entrapped chipping debris.

3. The device of claim 1, wherein the said femoral cutting guide comprises a polygonal body positioned and firmly secured against a femoral bone by two or more large guide wires passing through said guide into said femoral bone.

4. The device of claim 1, wherein the said femoral cutting guides comprises T grooves to slidably accept inverted T shaped rails running longitudinally along the bottom of said hollow casting body whereby movement of said hollow casting body is thereby guided during the bone chipping process.

5. The device of claim 1, wherein said tibial cutting guide comprises a template having a polygonal body positioned and firmly secured against a tibial bone by two or more large pins or guide wires passing through said templates and driven into the lateral aspect of the tibial bone.

6. The device in claim 1, wherein said tibial cutting guides comprises T grooves to slidably accept inverted T shaped rails running longitudinally along the bottom of said hollow casting body whereby movement of said hollow casting body is thereby guided during the bone chipping process.

* * * * *